United States Patent
Duraffourg et al.

(10) Patent No.: US 9,599,495 B2
(45) Date of Patent: Mar. 21, 2017

(54) THERMAL FLOW SENSOR WITH VIBRATING ELEMENT AND GAS SENSOR COMPRISING AT LEAST ONE SUCH SENSOR

(71) Applicant: COMMISSARIAT A L'ENERGIE ATOMIQUE ET AUX ENE ALT, Paris (FR)

(72) Inventors: Laurent Duraffourg, Voiron (FR); Philippe Andreucci, Moirans (FR); Eric Colinet, Grenoble (FR); Guillaume Jourdan, Grenoble (FR); Julien Arcamone, Grenoble (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 779 days.

(21) Appl. No.: 14/030,205

(22) Filed: Sep. 18, 2013

(65) Prior Publication Data

US 2014/0076024 A1    Mar. 20, 2014

(30) Foreign Application Priority Data

Sep. 19, 2012  (FR) ..................... 12 58795

(51) Int. Cl.
   *G01N 27/18*     (2006.01)
   *G01F 1/66*      (2006.01)
   (Continued)

(52) U.S. Cl.
   CPC ............ *G01F 1/662* (2013.01); *G01N 25/18* (2013.01); *G01N 27/18* (2013.01); *G01N 29/022* (2013.01);
   (Continued)

(58) Field of Classification Search
   CPC ............................. G01N 30/66; G01N 27/18
   See application file for complete search history.

(56) References Cited

U.S. PATENT DOCUMENTS

2007/0222011 A1   9/2007 Robert et al.
2008/0314148 A1  12/2008 Robert
                  (Continued)

FOREIGN PATENT DOCUMENTS

EP   1 840 582 A1   10/2007
FR   2 917 731 A1   12/2008
                  (Continued)

OTHER PUBLICATIONS

U.S. Appl. No. 14/619,656, filed Feb. 11, 2015, Ruellan, et al.

(Continued)

*Primary Examiner* — Laura Martin
*Assistant Examiner* — Alex Devito
(74) *Attorney, Agent, or Firm* — Oblon, McClelland, Maier & Neustadt, L.L.P.

(57) ABSTRACT

The invention relates to a thermal flow sensor comprising:
   a support,
   at least one element intended to be vibrated relative to the support,
   suspension means for said vibrating element relative to the vibrating element,
   means for heating the vibrating element,
   means for electrostatic excitation of the vibrating element so as to vibrate it at its resonance frequency,
   piezoelectric gauges for detecting the resonance frequency variation of the vibrating element, the gauges forming means for heating the vibrating element by Joule effect and the suspension means comprising two beams formed by nanowires so as to reduce the heat losses from the vibrating element toward the support.

30 Claims, 10 Drawing Sheets

(51) Int. Cl.
  *G01N 33/00* (2006.01)
  *G01N 25/18* (2006.01)
  *G01N 29/02* (2006.01)
  *G01N 30/66* (2006.01)
(52) U.S. Cl.
  CPC ......... *G01N 30/66* (2013.01); *G01N 33/0027* (2013.01)

(56) References Cited

U.S. PATENT DOCUMENTS

2011/0077872 A1   3/2011   Loui et al.
2013/0170517 A1   7/2013   Duraffourg et al.
2014/0318906 A1   10/2014  Deimerly et al.

FOREIGN PATENT DOCUMENTS

FR           2 965 349 A1     3/2012
WO    WO 2011/154363 A2      12/2011

OTHER PUBLICATIONS

Search Report issued Oct. 9, 2013, in European Patent Application No. 13185043.0 (with English Translation of Category of Cited Documents).

Xiaobo Guo, et al., "Gas Sensing Using Thermally Actuated Dual Plate Resonators and Self-Sustained Oscillators", Frequency Control Symposium, XP 032205290, May 21, 2012, 5 pages.

D. Mercier, et al., "Characterization of a SAW-Pirani vacuum sensor for two different operating modes", Sensors and Actuators A, vol. 188, XP 055082098, Feb. 1, 2012, pp. 41-47.

S. Fanget, et al., "Gas sensors based on gravimetric detection—A review", Sensors and Actuators B, vol. 160, 2011, pp. 804-821.

I. Bargatin, et al., "Efficient electrothermal actuation of multiple modes of high-frequency nanoelectromechanical resonators", Applied Physics Letters, vol. 90, 2007, pp. 093116-1-093116-3.

Bradley C. Kaanta, et al., "A monolithically fabricated gas chromatography separation column with an integrated high sensitivity thermal conductivity detector", Journal of Micromechanics and Microengineering, vol. 20, 2010, 6 pages.

Behzad Razavi, "A Study of Phase Noise in CMOS Oscillators", IEEE Journal of Solid-State Circuits, vol. 31, No. 3, Mar. 1996, pp. 331-343.

E Mile, et al., "In-plane nanoelectromechanical resonators based on silicon nanowire piezoresistive detection", Nanotechnology, vol. 21, 2010, 7 pages.

J. F. Creemer, et al., "MEMS Hotplates with TiN as a Heater Material", IEEE $4^{th}$ Conference on Sensors, 2005, pp. 330-333.

J. F. Creemer, et al., "Microhotplates with TiN heaters", Sensors and Actuators A, vol. 148, 2008, pp. 416-421.

K. Khosraviani, et al., "Low-Cost Surface Micromachined Pirani Pressure Sensor with Atmospheric pressure Range", Electrical and Computer Engineering, CCECE Canadian Conference, 2007, pp. 153-156.

R. Puers, et al., "The NanoPirani—an extremely miniaturized pressure sensor fabricated by focused ion beam rapid prototyping", Sensors and Actuators A, vol. 97-98, 2002, pp. 208-214.

French Preliminary Search Report issued Jan. 10, 2013, in Patent Application No. FR 1258795, filed Sep. 19, 2012 (With English Translation of Category of Cited Documents).

J. Arcamone, et al., "VLSI silicon multi-gas analyzer coupling gas chromatography and NEMS detectors", IEEE International Electron Devices Meeting (IEDM), XP 032096029, Dec. 5, 2011, pp. 669-672.

Nickolay V. Lavrik, et al., "Cantilever transducers as a platform for chemical and biological sensors", Review of Scientific Instruments, vol. 75, No. 7, XP 012071658, Jul. 2004, pp. 2229-2253.

Han Ji-Song, et al., "Fabrication of thermal-isolation structure for microheater elements applicable to fingerprint sensors", Sensors and Actuators A, vol. 100, No. 1, XP 004373768, Aug. 15, 2002, pp. 114-122.

Office Action issued Oct. 20, 2016 in European Patent Application No. 13185043.0.

Ashish Kumar Namdeo, et al., "FEM Study on Contactless Excitation of Acoustic Waves in SAW Devices", Proceedings of the 2009 COMSOI, Conference, Nov. 14, 2009, pp. 1-4.

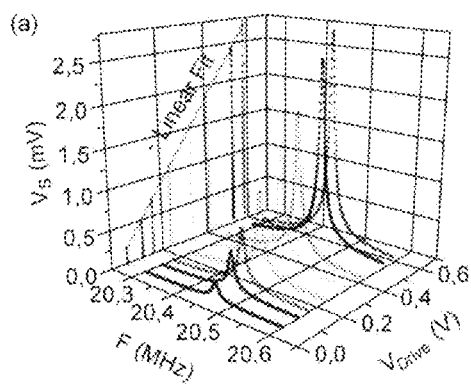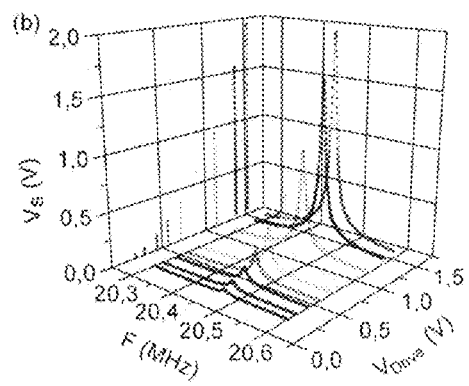
FIG.2A  FIG.2B
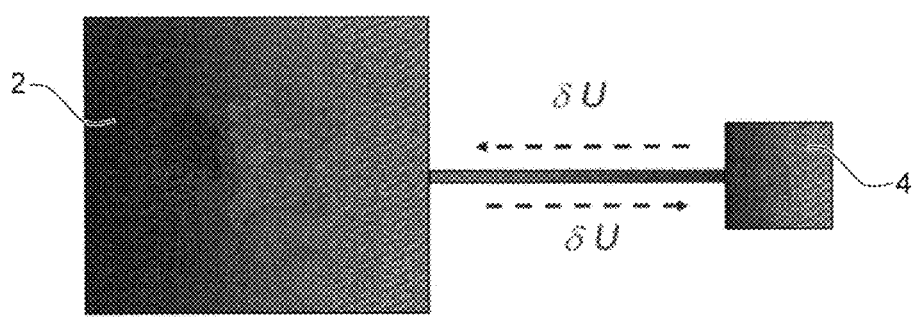
FIG.3 in # THERMAL FLOW SENSOR WITH VIBRATING ELEMENT AND GAS SENSOR COMPRISING AT LEAST ONE SUCH SENSOR

TECHNICAL FIELD AND BACKGROUND OF THE INVENTION

The present invention relates to a thermal flow sensor implementing at least one nanoelectromechanical resonator (or NEMS for "nanoelectromechanical system") or microelectromechanical resonator (or MEMS for "microelectromechanical system"), to determine the concentration of the components of a gas from its thermal characteristics, and to a gas sensor comprising at least one such sensor.

A thermal flow sensor refers to any sensor measuring a heat exchange between the body of the sensor and the fluid medium in which the sensor is positioned. This thermal flow sensor is for example a gas sensor or a pressure sensor.

A system capable of determining the analyte composition of a gas may be used to detect and quantify the analytes at the outlet of a chromatography column, more particularly a chromatography micro-column, the latter making it possible to temporarily separate the different gaseous elements of a complex mixture. The sensor serves to quantify the relative concentration of the analytes of the gas to be analyzed successively arriving on its surface. The analytes are mixed in a gas, called carrier gas, that is sent into a chromatography column and on the sensor at a fixed speed.

The carrier gas may be dry air or an inert gas, for example.

Several types of sensor exist that may be positioned at the outlet of the chromatography column.

Flame ionization detector (FID) sensors.

The gases to be analyzed are burned under a hydrogen flow creating ions and electrons. The charged particles are collected by electrodes and the generated current is measured using a picoammeter. On the one hand, the sensor only allows the detection of organic components. On the other hand, it requires a flow of hydrogen, and the produced quantity of ions remains low. Lastly, the size of the sensor cannot be reduced.

Optical sensors also exist, the operating principle of which is generally based on infrared absorption of an optical flow. The sensors are suitable for detecting carbonaceous elements. However, to be able to detect other types of gases, the number of laser sources would need to be multiplied, which would considerably increase the complexity and cost of such an apparatus. The sensors are also difficult to miniaturize.

Electronic sensors, the detection principle of which is based on varying an electrical property (electrical resistance, resistance, surface potential) induced by the presence of gas molecules on its surface. These sensors require surface functionalization. The macroscopic sensors are relatively insensitive. Micrometric or nanometric sensors suffer from drift problems, i.e., random long-term drifts in the property to be measured and extreme sensitivity to the initial surface states. They must also be functionalized.

Thermal conductivity detector (TCD) sensors also exist. A TCD may comprise a wire brought to a high temperature, the electrical resistance of which is measured. The wire has a given temperature for a given gas. When the gas changes, the properties of the thermal environment (thermal conductance, viscosity, heat convection) change, which causes a variation in the temperature of the wire. This variation in turn causes a change of electrical resistance that is detected through a measurement bridge. The higher the temperature of the TCD sensor, the better its resolution. It is therefore necessary to work in an oxygen-free environment to prevent the wire from burning. Generally, the TCD wire must be placed under a helium carrier gas flow or hydrogen carrier gas flow. Using a rare gas makes it possible to have a considerable contrast relative to the air. This represents a significant limitation of the detector. Furthermore, a major contrast of thermal constants exists between these light gases and the analytes to be detected, which makes the system more sensitive than under a simple flow of dry air.

Gravimetric sensors also exist. They involve measuring the mass quantity of the target gas adsorbed at the surface of the sensor.

Generally, the sensor is a system vibrating at a unique oscillation frequency. The oscillation frequency shift of the system is measured, which results from the addition of mass, also called gravimetric effect, toward the low frequencies caused by the adsorption of the gas. The surface of the sensor is functionalized to sense the gas. These sensors have a high sensitivity for large gaseous molecules, but a lower concentration measurement sensitivity for very light and/or volatile molecules. This type of sensor is described in the document Fanget, S. Hentz, P. Puget, J. Arcamone, M. Matheron, E. Colinet, P. Andreucci, L. Duraffourg, E. Myers, M. L. Roukes, "*Gas sensors based on gravimetric detection—A review*", Sensors and Actuators, B: Chemical, 160(1), 2011, 804-821.

BRIEF DESCRIPTION OF THE INVENTION

It is consequently one aim of the present invention to offer a thermal flow sensor that offers high sensitivity and can be miniaturized.

The aim of the present invention is achieved by a thermal flow sensor comprising a vibrating element that can be vibrated by excitation means, means for heating said vibrating element, and means for measuring the frequency variation of the vibrating element so as to determine the temperature variation and thus a thermal flow.

The vibrating element is positioned in the gas to be analyzed. The vibrating element is suspended relative to a support so as to limit the heat losses from the vibrating element toward the support. The suspension means then form thermal insulation means. Advantageously, the suspension and thermal insulation means are formed by beams of the nanowire type.

In one embodiment, the heating means are in contact with the vibrating element, that contact being electrical and mechanical.

In another embodiment, the heating means are situated away from the vibrating element, the latter being heated by thermal conduction through the gas to be analyzed.

In other words, the variation of the vibration frequency of the vibrating element is measured, which is caused by the temperature variation of the vibrating element due to the thermal exchanges with the surrounding gas. From this vibration frequency variation, it is possible to determine the heat flows between the vibrating element and the gas, and to deduce therefrom the composition of the gas that is responsible for those thermal exchanges, in the case of a gas sensor.

The sensor has the advantage of being insensitive to mass absorption, since, due to the heating of the vibrating element, the absorbed mass is immediately desorbed and does not have any impact on the oscillation frequency variation of the vibrating element.

The subject-matter of the present invention is a thermal flow sensor comprising:

a support,
at least one element intended to be vibrated relative to the support, called vibrating element,
suspension and thermal insulation means for insulating said vibrating element relative to the support,
means for heating the vibrating element,
means for exciting the vibrating element so as to vibrate it at its resonance frequency,
means for detecting the resonance frequency variation of the vibrating element.

The suspension and thermal insulation means advantageously comprise at least one beam dimensioned such that the heat losses through the suspension means from the vibrating element toward the support are reduced. The sizing of the beam consists of choosing its section, length, shape, etc.

In one example embodiment, the suspension and thermal insulation means comprise at least two beams aligned on either side of the vibrating element or inclined relative to one another and having a common link to the vibrating element.

Very advantageously, the beam has a section comprised between $10 \times 10$ nm$^2$ and $250 \times 250$ nm$^2$, and preferably equal to $50 \times 50$ nm$^2$.

The beam may have a nonlinear shape, advantageously a serpentine shape or a shape with at least one rectangle that is hollow between two segments.

Preferably, the beam is made from a thermally insulating material, for example amorphous silicon or another material.

Very advantageously, the suspension and thermal insulation means comprise a zone for anchoring to the support, formed by a nanostructured material, and the holes thus formed may or may not be filled in.

The heating means are for example heating means by Joule effect.

In another example embodiment, the heating means are in direct contact with the vibrating element.

The heating means may be formed by at least one electrically conducting element connected to a polarization source and the vibrating element.

The detection means may be formed by at least one piezoresistive gauge mechanically connected to the vibrating element. Advantageously, at least one piezoresistive gauge forms the Joule effect heating means.

In another example embodiment, the heating means are situated separated from the vibrating element, the heating being obtained by conduction through the gaseous environment between the heating means and the vibrating element. The heating means can be formed by a suspended wire.

The two vibrating elements may be positioned on either side of the heating means so as to perform a differential measurement.

In one example, the vibrating element is a vibrating element according to volume deformation modes.

In another example, the vibrating element is a rotational vibrating element.

The detection elements may comprise two piezoresistive gages providing a differential measurement. In another example embodiment, the detection means are capacitive detection means.

The excitation means may be electrostatic excitation means.

The subject-matter of the present invention is also a thermal flow measuring system comprising a plurality of sensors according to the present invention.

The subject-matter of the present invention is also a system for determining the concentration of a gaseous environment comprising at least one thermal flow sensor according to the present invention or a system according to the present invention, electronics for processing the electrical voltage values delivered by the thermal flow sensor.

The at least one sensor may be placed in an electronic oscillating and frequency- or phase-measuring loop.

The subject-matter of the present invention is also a device for analyzing a gas or mixture of gases comprising a gas chromatography column and at least one system for determining the concentration according to the present invention, said determination system being positioned in a channel connected to the outlet of the gas chromatography column.

BRIEF DESCRIPTION OF THE DRAWINGS

The present invention will be better understood using the following description and appended drawings, in which:

FIGS. 2A and 2B are graphic illustrations of examples of electric resonance signals of the vibrating element obtained using the sensor of FIG. 1, FIG. 3 is an illustration of a thermal model applicable to the sensor of FIG. 1.

DETAILED DESCRIPTION OF THE INVENTION

Figure 1:
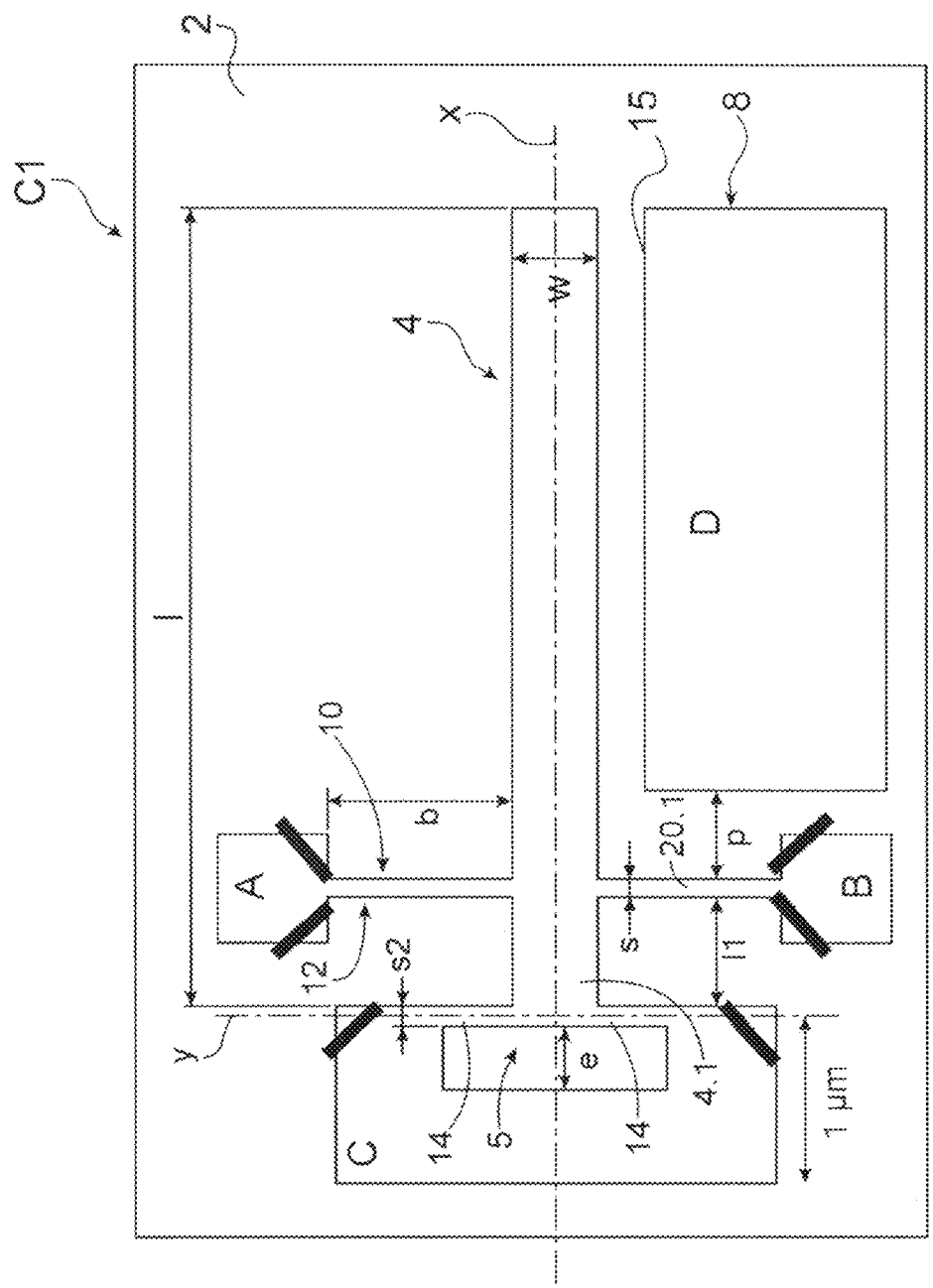
FIG. 1 is a diagrammatic top view of a first embodiment of a thermal flow sensor.

FIG. 1 shows a top view of one embodiment of a thermal flow sensor C1 comprising a stationary part 2 and a moving part 4. The stationary part 2 is for example formed by a support formed by a substrate in the microelectronic domain. The moving part 4 is formed by an element capable of oscillating relative to the substrate 2. The moving part 4 will be designated "vibrating element" in the rest of the description. The vibrant element 4 is, in the illustrated example, formed by a beam with a longitudinal axis X connected to one longitudinal end 4.1 of the substrate 2 by suspension means 5.

The sensor C1 also comprises means 8 for exciting the vibrating element 4, means 10 for heating the vibrating element 4, and means 12 for detecting the vibration of the vibrating element 4.

The suspension means 5 are such that they provide thermal insulation of the beam relative to the support.

Advantageously, the suspension means have a reduced conductance, thereby reducing the heat losses from the vibrating element 4 toward the substrate 2. In the illustrated example, the suspension means are formed by two aligned beams 14 with longitudinal axis Y perpendicular to the axis X of the vibrating element 4 and extending on either side of the vibrating element 4 at its longitudinal end 4.1. The beams 14 are suspended by their other longitudinal end at an anchoring stud C that may optionally form the electrical contact stud. In the illustrated example, the anchoring stud C is in the shape of a C.

The beams 14 have a small section; advantageously, they are formed by a nanowire. The beams 14 have a section preferably comprised between $10 \times 10$ nm$^2$ and $250 \times 250$ nm$^2$. Thus, the heat losses from the vibrating element toward the substrate 2 are limited by the section of the beams 14.

It is also possible to use thermally insulating materials such as amorphous silicon, which has a heat conductivity 4 W·m$^{-1}$·K$^{-1}$ compared to that of monocrystalline silicon, which is 148 W·m$^{-1}$·K$^{-1}$, or an insulator such as SiN whereof the heat conductivity is 2 W·m$^{-1}$·K$^{-1}$.

Figure 11:
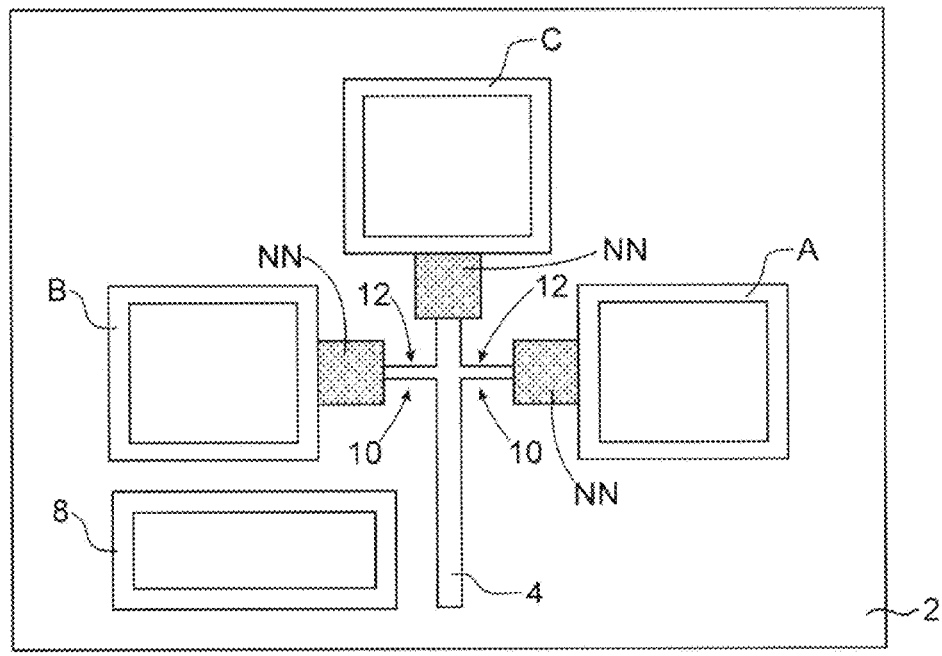
FIG. 11 is a top view diagrammatically showing an alternative embodiment in which the anchors are nanostructured.

Advantageously, it is possible to further improve the thermal insulation of the suspensions by nanostructuring the part of the support that serves as a mechanical anchor to the suspensions. In fact, by for example forming nanometric holes, for example in silicon, of approximately 20 nm in diameter with a pitch of from 15 nm to 20 nm, it is possible to block the diffusion of the heat while preserving the good electrical conduction properties. Thus, the embeddings of the suspensions become thermally insulating, but remained conductive for the electrons (or the holes). As an example, a monocrystalline silicon nanostructured in this way exhibits heat conductivity levels as low as amorphous silicon. FIG. 11 provides an example of such NN embeddings. These insulating means are called phononic insulators.

It is possible to consider filling in the holes with an insulating material such as SiO$_2$ or SiOC, or even SiN, which may be advantageous from a mechanical perspective by reinforcing the anchorings.

Alternatively, it is also possible to produce an embedding zone made from a material that is both thermally and electrically insulating, for example by using SiN or SiO$_2$.

This type of insulation is particularly adapted to silicon or SiGe or Ge.

The excitation means 8 are of the electrostatic type and comprising an electrode 15 designated D fixed on the substrate and across from a side face of the vibrating element 4. By applying a voltage difference between the electrode 15 and the vibrating element 4, the latter is vibrated at its resonance frequency.

The vibrant element 4 is then vibrated by the excitation means so as to pivot around an axis Z perpendicular to the axes X and Y.

In the illustrated example, the means 12 for detecting the vibration of the vibrating element 4 are formed by two strain gauges 20.1, 20.2 positioned on either side of the longitudinal axis X suspended between the vibrating element 4 and the anchoring studs A, B advantageously forming contact studs. Thus, the rotational movement of the vibrating element 4 around the axis X causes a deformation of the gauges 20.1, 20.2, that deformation being representative of the movement of the vibrating element 4.

The gauges 20.1, 20.2 are for example piezoresistive gauges. An electrical resistance variation is then measured within the gauges 20.1, 20.2 that is proportional to the strain applied to the gauges. The gauges 20.1, 20.2 are polarized between the studs A and B, and their electrical resistance variation causes a variation in the output voltage between the stud C and the ground.

In the illustrated example, the gauges form differential measuring means making it possible to eliminate outside variations, for example slow temperature variations of the environment. Alternatively, the detection means may comprise only one of the two gauges 20.1, 20.2.

Advantageously, the gauges are situated as close as possible to the axis of rotation where the stresses caused by the movement of the beam are maximal.

In the illustrated example, the heating means 10 are formed very advantageously by the gauges 20.1, 20.2 themselves. The heating of the vibrating element 4 is obtained by Joule effect within the gauges and by conduction. The polarization of the gauges used to measure the detection is then used as heating means, which makes it possible to simplify the sensor.

Alternatively, the suspension beams may serve as Joule effect heating means, the suspension means then being electrically conductive. In order to reduce the heat losses thereof, the embeddings are advantageously nanostructured.

Alternatively, it is possible to consider adding heating means of the nanowire type separate from the gauges in the beams, but the addition of such nanowires results in reducing the strains in the gauges and therefore the measured signal.

The heating temperature of the vibrating element is for example comprised between 300° C. and 1000° C.

The gauges advantageously have a small section so as to concentrate the strain undergone and increase the mechanical response. Furthermore, the small section makes it possible to limit the heat losses of the vibrating element 4 toward the substrate 2. Preferably, the gauges have a section comprised between $10 \times 10$ nm$^2$ and $250 \times 250$ nm$^2$ for lengths between 100 nm and 500 nm.

It is also possible to consider increasing the thermal insulation by nanostructuring the embedding zone of the gauges in the same way as the embedding studs of the suspension means described in FIG. 11.

Figure 12:
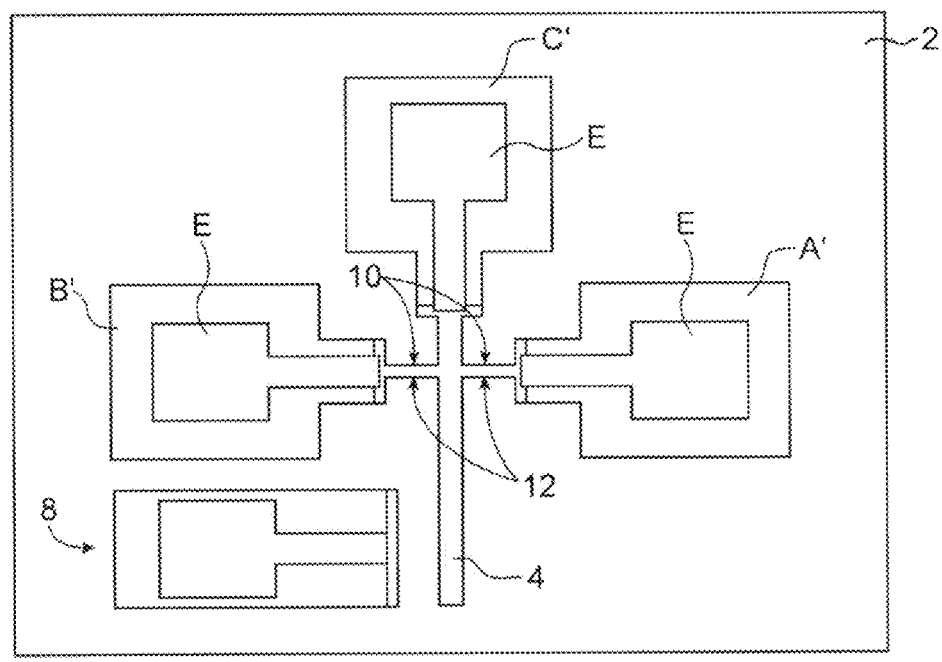
FIG. 12 is a top view diagrammatically showing another alternative embodiment according to which the insulating anchors are covered with a conductive layer.

FIG. 12 shows an example embodiment in which the embeddings A', B', C' are done in a thermally and electrically insulating material, such as SiN or SiO$_2$. In this alternative, the embeddings A', B', C' are covered with a thin layer of electrically conductive material E, preferably a metal, the thickness of which remains very small, for example less than 10 nm. Preferably, this metal will be TiN or AlSi. The thermal flow toward the support is therefore limited.

Preferably, the suspensions, the gauges in the case of the piezoresistive detection mode, and the vibrating element are made from a monocrystalline silicon. Nanowires are then favored to produce the gauges and the suspensions and/or insulating anchoring of the nanostructured anchoring type.

Examples of characteristic dimensions of the sensor are provided in the below table:

| w | L | l1 | b | s | s2 | e | p | g |
|---|---|---|---|---|---|---|---|---|
| 300 nm | 3.2 μm | 480 nm | 300 nm | 100 nm | 120 nm | 250 nm | 250 nm | 150 nm |
| 300 nm | 3.2 μm | 480 nm | 600 nm | 100 nm | 120 nm | 250 nm | 250 nm | 150 nm |
| 300 nm | 7 μm | 1.05 μm | 600 nm | 100 nm | 150 nm | 250 nm | 250 nm | 150 nm | w is the width of the vibrating element 4;
l is the length of the vibrating element 4;
l1 is the distance between the gauges 20.1, 20.2 in the beam 14;
b is the length of the gauges 20.1, 20.2, approximately from 200 nm to 400 nm;
s is the width of the gauges 20.1, 20.2, typically comprised between 80 nm and 160 nm;
s2 is the thickness of the beams 14;
e is the distance between the anchoring stud C and the lateral edge across from the beams 14;
p is the distance between the gauge 20.1 and the electrode D;
g is the distance between the electrode and the lateral face facing the vibrating element 4.

Figure 4A:
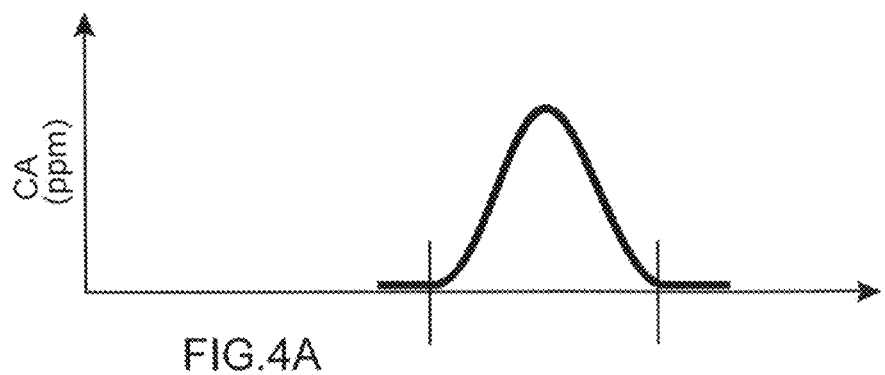
FIG. 4A is a graphic illustration of an analyte concentration variation as a function of time.
Figure 4B:
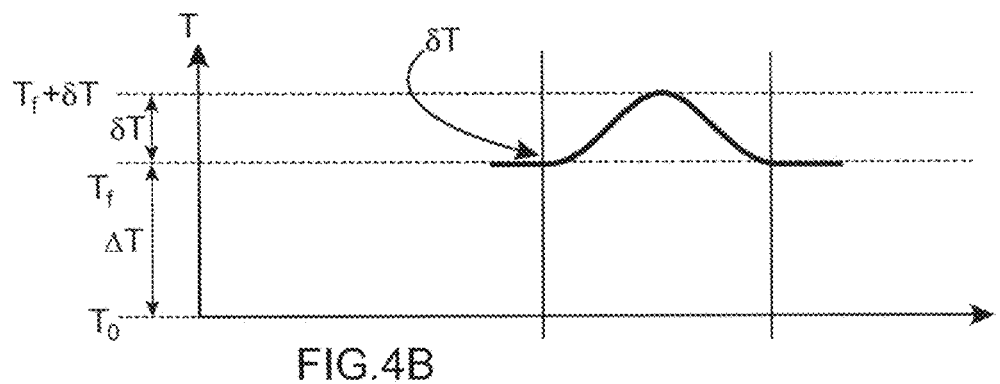
FIGS. 4B and 4C are graphic illustrations of temperature and frequency variations resulting from the concentration variation of FIG. 4A respectively measured for a sensor of FIG. 1.
Figure 4C:
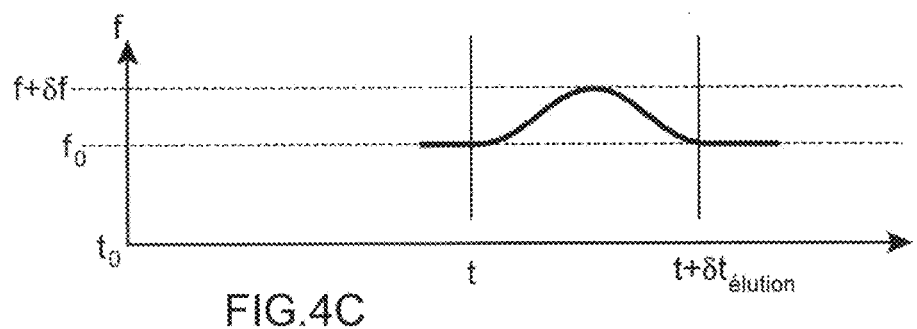

We will describe the operating principle of the sensor according to FIG. 1 in an application to the determination of the composition of a gaseous environment relative to the graphic illustrations of FIGS. 4A to 4C. The gaseous environment comprises a carrier gas, for example helium or dry air, and analytes; it is the analyte concentration we wish to determine.

FIG. 4A is a graphic illustration of an analyte concentration variation CA in ppm of the gas to be analyzed as a function of time.

FIG. 4B is a graphic illustration of the temperature variation T the concentration variation of FIG. 4A as a function of time of the vibrating element 4.

FIG. 4C is a graphic illustration of the resonance frequency variation f of the vibrating element 4 resulting from the concentration variation of FIG. 4A.

In the initial state $t_0$, the vibrating element 4 is heated by Joule effect to the temperature $T_0+\Delta T$ that is the operating temperature $T_f$, using gauges 20.1, 20.2. $\Delta T$ is chosen to minimize the effects of the conduction other than that which occurs in the gas that is the carrier gas. The operating temperature is chosen so as to optimize the signal-to-noise ratio and the coefficient α described below.

At a moment t, an analyte mixed with the carrier gas arrives on the sensor, thereby modifying the conduction properties of the surrounding gas designated $G_g$.

The considered fluidic time constants, i.e., the edge of the elution peak and the duration of that peak of approximately 100 ms, are large in light of the mechanical response, which is for example comprised between 0.1 μs and 1 μs, and the thermal response, which is for example less than 500 ns. As long as the analyte is present in the carrier gas, the conduction goes from $G_g$ to $G_g+\delta G$, which causes a temperature variation δT relative to the operating temperature $T_f$. This temperature variation causes a frequency shift. Furthermore, the strain varying with the vibrations, the frequency variation of the vibrations causes a variation of the strains, and the frequency of the electrical signal obtained by piezoresistive effect also varies.

When the analyte is no longer present in the carrier gas at the end of the elution peak, after a time $\delta t_{élution}$, the temperature returns to $T_f$. The sensor is ready to detect another analyte peak.

Figure 14:
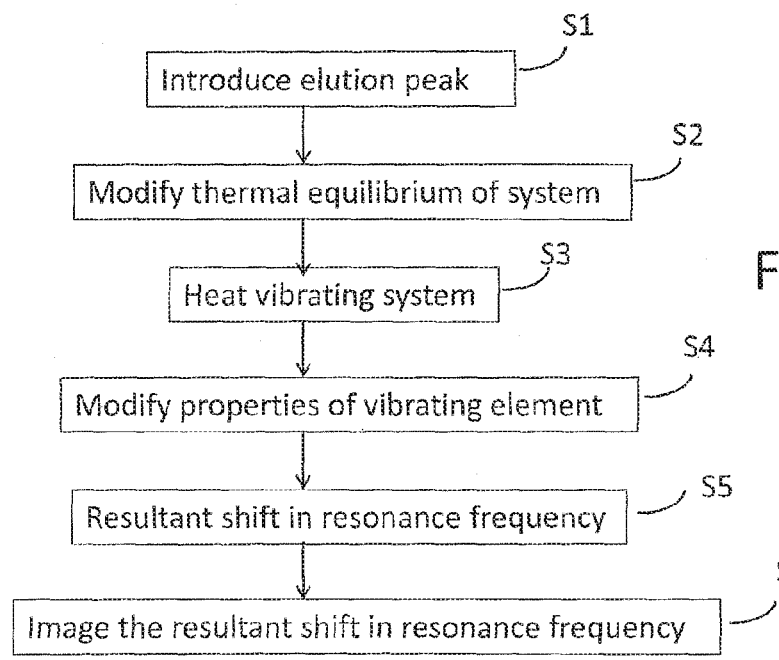
FIG. 14 shows a flowchart of the various steps of an example of a method for measuring the frequency variation of the vibrating element.

FIG. 14 shows a flowchart of the various steps of one example method for measuring the frequency variation of the vibrating element.

When an elution peak, corresponding to a gaseous analyte having a certain temporal width, for example 100 ms to several seconds in duration, and a certain spatial width, for example 1 mm, comes around the vibrating structure (step S1), the thermal equilibrium of the system is then modified (step S2). The diffusion of heat through the gas is then modified: the gaseous environment generally being less thermally conductive than the carrier gas (in the absence of analyte), the vibrating system heats up (step S3). In fact, the vibrating element being thermally insulated, i.e., there is little exchange with the silicon support, the temperature of the vibrating element is primarily fixed by the surrounding gas. When the vibrating element heats up, its mechanical properties (in particular the Young's modulus, Poisson ratio, strains) are modified (step S4), causing a shift of the resonance frequency of the mechanical system (step S5). The mechanical system having a significantly faster temporal response than that of the elution peak (1 ms versus 1 second) and faster than the thermal constant of the gas/silicon surface system (approximately 100 μs), the frequency is a perfect image of the elution peak (step S6). To perform the measurement, the vibrating system is integrated into a frequency measuring loop. This may be a phase-locked loop (PLL) or an auto-oscillating loop. The frequency is then monitored in real time.

The vibrating element 4 is excited by an electrostatic force at its resonance frequency $\omega_0$. The force $F_g$ acting on the gauges may be expressed as follows (in the frequency domain), considering an equivalent mass/spring model:

$$F_g(\omega) = \beta \frac{\omega_0^2}{\omega_0^2 - \omega^2 + j\omega\omega_0/Q} F_{el}(\omega)$$

β, ω, Q and $F_{el}(\omega)$ are the amplification factor of the lever arm produced by the beam, the angular frequency (rad/s), the quality factor, and the electrostatic force respectively applied between the electrode 15 and the vibrating element 4.

The electrostatic force is generated by an RF voltage designated $V_{drive}(\omega)$. It is also possible to provide for adding a direct voltage $V_{DC}$. In that case, since the force is proportional to the voltage squared, the alternating excitation signal has a frequency equal to the resonance frequency of the beam. If the excitation frequency only has an alternating component, its frequency is the resonant frequency divided by 2. Both cases are possible. An excitation at 2 w has the advantage of having less continuous background.

One of the gauges 20.1, 20.2 is compressed and the other gauge 20.2, 20.1 is simultaneously stretched under the strain $F_g$/s, s being the section of the gauges.

The resistance variation ΔR by piezoresistive effect in the gauges 20.1, 20.2 is therefore expressed as follows:

$$\frac{\Delta R(\omega)}{R} = \gamma \frac{F_g(\omega)}{2 \cdot s \cdot E}$$

γ and E are the gauge factors and the Young's modulus of the gauges. The value of G depends on the material used for the gauges, for example the type of semiconductor, and its doping. G is generally comprised between 10 and 100.

The output voltage $V_s$ on C relative to the mass is expressed:

$$V_s(\omega) \propto \frac{\gamma \beta V_{bias} V_{DC} V_{drive}(\omega)}{2 \cdot s \cdot E} \frac{Q\omega_0^2}{\sqrt{(\omega_0^2 - \omega^2)^2 + \omega^2 \omega_0^2}}$$

$V_s$ is proportional to the bias voltage and the RF voltage. If the DC voltage is not used, $V_s$ will be proportional to the square of the RF voltage.

Preferably, the bias voltage is an alternating voltage making it possible to perform a heterodyne measurement, i.e., making it possible to have a different detection frequency from the excitation frequency, which may make it possible to work at high excitation frequencies.

The vibrating element 4 is resonated and the variation of the resonance frequency of the vibrating element is monitored. FIGS. 2A and 2B show examples of the variation of the voltage Vs as a function of the bias voltage and the voltage as a function of the voltage $V_{drive}(\omega)$ respectively at the resonance frequency of the vibrating element.

The effect of the temperature of the vibrating element on its resonance frequency will now be described.

Let us consider the resonance frequency variation as a function of the temperature. It is known that, for a given operating point ($T_0$), the resonance frequency of the materials, for example for semiconductor materials, varies proportionally with the temperature. This variation is written:

$$\omega_0(T) = \omega_0(T_0)(1 + \alpha \Delta T)$$

$$\mathfrak{R} \equiv \alpha = \frac{1}{\omega_0(T_0)} \frac{d\omega}{dT}$$

α is the heat coefficient, and ΔT is the temperature variation relative to $T_0$. In the case of silicon, α is approximately—100 ppm at a temperature of 300 K. α constitutes the heat response $\mathfrak{R}$ of the system, the frequency being the measuring parameter.

Heat exchangers exist between the vibrating element 4 and its environment.

It is desirable to know the temperature of the vibrating element at all times by considering that the latter exchanges heat through the surrounding gas and with the mechanical supports through the beams 14 and the gauges.

Upon first approximation, a 1D model of the thermal RC type diagrammed in FIG. 3 is used. Given the considered dimensions, the convection phenomena on the vibrating element 4 with or without a cover on the sensor are negligible. Only the conduction will be considered.

δU represents the internal energy exchange between the heat reservoir having a fixed temperature, forming a thermostat, made up of the substrate 2, and the heat capacity of the vibrating element 4, designated C.

The heat diffusion equation of the system is written as follows:

$$C \frac{d\Delta T}{dt} + G \Delta T = P(t)$$

G is the conductance via the gas and the solid mechanical connections formed by the gauges 20.1, 20.2 and the beams 14. P(t) is the thermal power contributed on the system. ΔT is the temperature elevation of the vibrating element 4.

In the embodiment of FIG. 1, the thermal power is generated through the gauges 20.1, 20.2 by Joule effect. The reading voltage $V_{bias}$, which is generally alternating, may serve to produce the heat necessary to heat the sensor by self-heating. A dedicated direct voltage $V_{chauffe}$ may be superimposed on this reading voltage $V_{bias}$. By specifying the notations and outlining the expressions, the preceding equation becomes:

$$C \frac{d\Delta T}{dt} + (G_g + G_{jauges} + G_{encastrements})\Delta T = \frac{V(t)^2}{R_{jauges}}$$

with V (t)=$V_{bias}$+$V_{chauffe}$ or V (t)=$V_{bias}$. R is the electrical resistance of the gauges.

Let us consider that V(t)=$V_0$H(t-$t_0$) or H(t-$t_0$) is the Heaviside function. This equation may be resolved by considering the static part on the one hand and the transient part on the other hand. The transient part corresponds to an increasing time constant exponential:

$$\tau_{th} = C/(G_g + G_{jauges} + G_{encastrement}).$$

The temperature increase ΔT in the stable state corresponds to:

$$\Delta T = V_0^2 / R_{jauges}(G_g + G_{jauges} + G_{encastrement}).$$

$V_0$ is the RMS voltage of the signal if the latter is alternating.

As a result, the frequency response of the system to the temperature increment is therefore (in Hz or rad·s$^{-1}$):

$$\Delta \omega = \frac{\alpha \omega_0 V_0^2}{R_{jauges}(G_g + G_{jauges} + G_{encastrements})}$$

By choosing gauges and embeddings having very low thermal conductivities, the frequency thermal response of the system Δω is maximized. Furthermore, this relationship shows that, preferably, the thermal conductivities of the gauges and the embeddings thereof will be chosen to be as low as possible so as to best see the effect of the variation of the thermal conductivity of the gas. From this resonance frequency variation, it is possible to go back to the temperature variation of the vibrating element and deduce the composition of the peak therefrom.

To monitor the frequency variation of the vibrating element 4, the sensor is placed in an electronic oscillating and frequency or phase measuring loop. The sensor may be placed in a phase-locked loop (PLL) or an auto-oscillating loop. The resolution of the assembly formed by the sensor and electronics therefore depends on its frequency stability, i.e., the fluctuation of the frequency $\sigma_\omega$ over time around the nominal frequency:

$$\sigma_\omega^2 = \frac{S_\omega(\omega = \omega_0)}{\tau}$$

The frequency resolution, which is the smallest measurable frequency set by the noises intrinsic to the system, and the temperature resolution, are respectively:

$$\delta\omega = \sqrt{\frac{\left(\frac{\omega_0^2}{4Q^2}\frac{1}{SNR^2} + \frac{\omega_0 \alpha k_B \cdot T^2}{(G_{jauges} + G_{encastrements})}\right)}{\tau}}$$

$$\delta T = \mathfrak{R}^{-1}\sqrt{\frac{\left(\frac{\omega_0^2}{4Q^2}\frac{1}{SNR^2} + \frac{\omega_0 \alpha k_B \cdot T^2}{(G_{jauges} + G_{encastrements})}\right)}{\tau}}$$

$$\delta T = \frac{\sqrt{\left(\frac{\omega_0^2}{4Q^2}\frac{1}{SNR^2} + \frac{\omega_0 \alpha k_B \cdot T^2}{(G_{jauges} + G_{encastrements})}\right)}}{\alpha\sqrt{\tau}}$$

These resolutions are optimized with the working temperature, the reading and actuating voltages of the system, the choice of the material (in particular the parameters: the temperature coefficient α, the electrical resistance R and the Young's modulus E varying differently depending on the selected material) and the morphology of the sensor. As described above, the thermal conductance is defined by insulating the beam from the support and choosing a suitable material.

Different transduction methods may be chosen so as to minimize the noise, for example a capacitive measurement instead of using piezoresistive gauges for this type of vibrating gauge.

Figure 5:
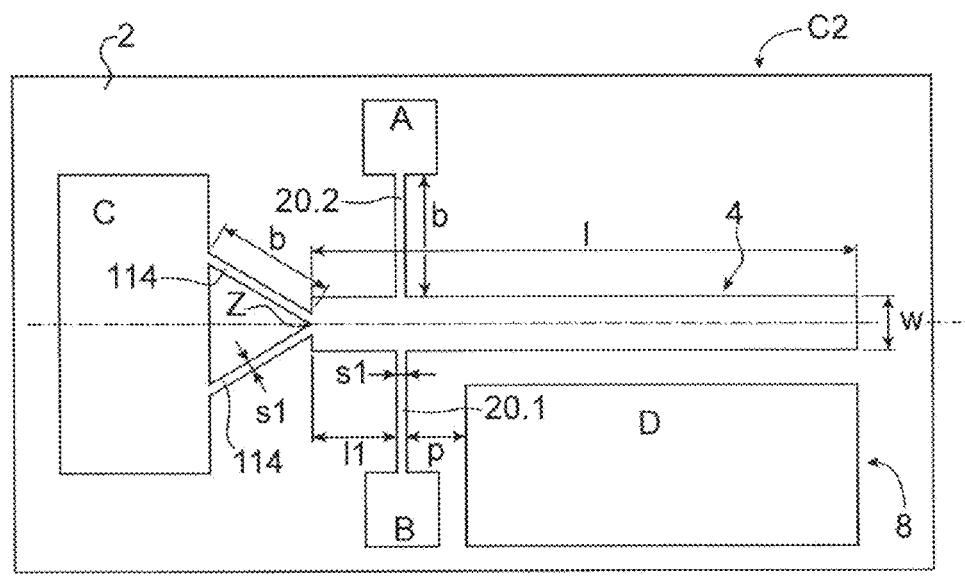
FIG. 5 is a diagrammatic top view of an alternative embodiment of a sensor according to the first embodiment.

FIG. 5 shows one alternative embodiment of a sensor according to the first embodiment. The latter C2 differs from the sensor of FIG. 1 by the shape of the suspension means.

The same references will be used to describe the elements performing the same function and having a close or similar structure.

The sensor of FIG. 5 comprises an element 4 vibrating relative to a substrate 2 by suspension means formed by two beams 114 connected by a first longitudinal end to the anchoring stud C and by a second longitudinal end to the longitudinal end 4.1 of the moving element. The beams 114 differ from the beams 14 in that their longitudinal axes are inclined relative to the axis X and are concurrent at their second longitudinal end with the axis Z. In the illustrated example, the beams 114 are inclined by an angle of 45° relative to the longitudinal axis X.

In the examples of FIGS. 1 and 5, the suspension means comprise two beams. It is also possible to consider that they comprise one beam or more than two beams.

Figure 6A:
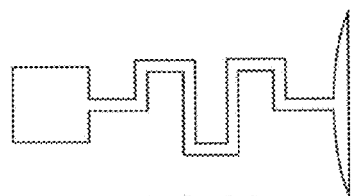
FIGS. 6A to 6C are alternative embodiments of suspension means adapted to suspend a vibrating element for a sensor according to the invention.
Figure 6B:
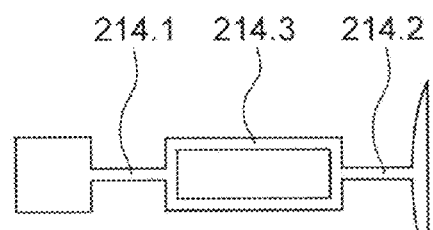
Figure 6C:
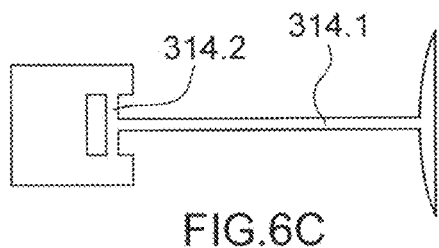

In FIGS. 6A to 6C, other example embodiments are shown of suspension means suitable for suspending the vibrating element relative to the substrate.

In FIG. 6A, the beam is in the shape of a slot. In FIG. 6B, the beam comprises two straight portions 214.1 connected by a frame-shaped portion 214.2. This embodiment makes it possible to reduce the heat losses very effectively and to absorb the expansion effects.

In FIG. 6C, the suspension means comprise a straight beam 314.1 connected to the substrate 2 by a suspended beam 314.2 perpendicular to the straight beam 314.1.

It will be understood that the different examples of suspension means may be combined, for example the slot-shaped beam 6A or that of FIG. 6B may be connected to the substrate by a transverse beam of FIG. 6C.

Furthermore, the suspension means may be formed by several beams of FIGS. 6A to 6C.

The suspension elements 14 (FIG. 1), 114 (FIG. 5) are small beams that are part of the anchor. They are of the nanowire type with a width substantially equal to that of the gauges (for example, approximately 100 nm), smaller than the width of the suspended beam forming the vibrating sensor.

Figure 7:
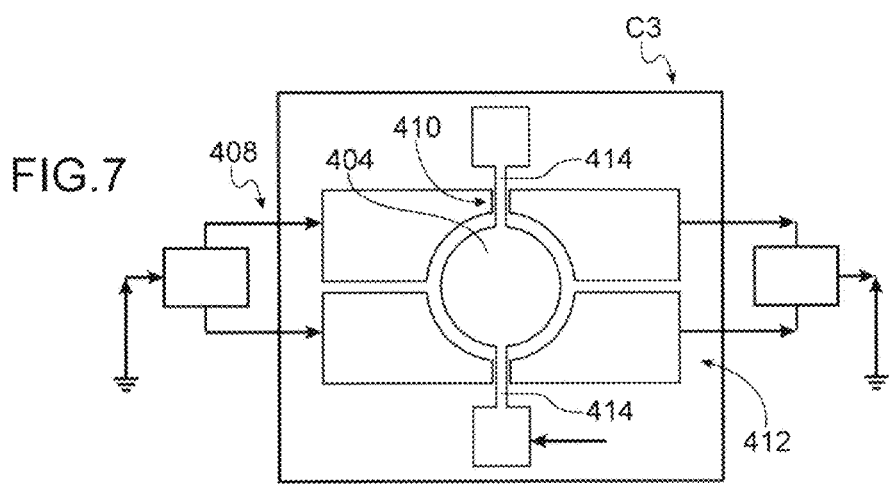
FIG. 7 is a diagrammatic top view of another example embodiment of a sensor according to the first embodiment, the vibrating element vibrating according to volume deformation modes.

In the case where the vibrating element is formed by a disc or plate, the anchors may be formed by beams or an assembly of beams (FIGS. 6A to 6B and FIG. 7). Their dimensions are preferably smaller than 500 nm wide for lengths greater than 1 μm.

Figure 6D:
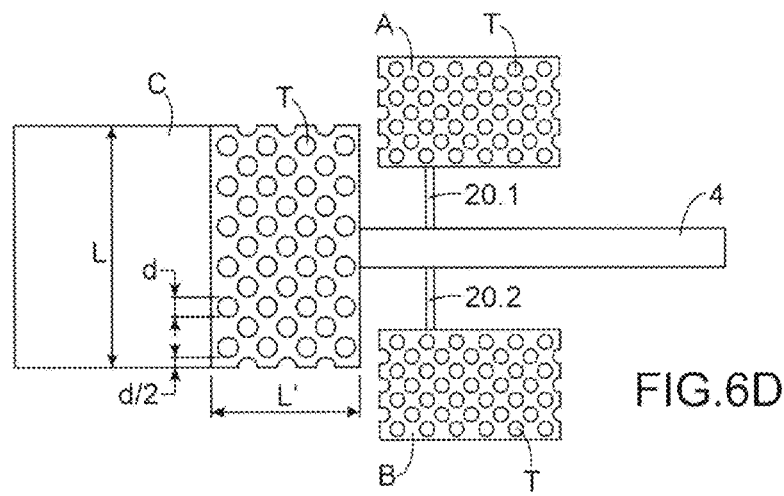
FIG. 6D is a diagrammatic top view of one example embodiment of the sensor with anchors provided with holes.

In FIG. 6D shows an example of anchors for the suspension elements of a vibrating element in the form of a plate/disc or beam. The anchors A, B, C are provided with holes 15 making it possible to still further improve the thermal insulation. Their diameter is for example approximately or smaller than 250 nm and may reach 10 nm for an edge-to-edge distance of approximately 100 nm. The anchors A and B comprise holes over their entire surface, and the anchor C comprises holes over part of its surface on the side of the connection to the suspended beam. This part has a width L', and the holes have a diameter d.

The table below shows examples of dimensions for the diameter d of the holes and the width L' of the structured part of the anchor C, for a width L of the anchor C of 10 μm.

| L'(μm) | d(nm) |
|---|---|
| 20 | 50 |
| 20 | 100 |
| 50 | 200 |
| 50 | 250 |
| 100 | 250 |

In the example of FIGS. 1 and 5, the vibrating element is formed by a beam. According to another example embodiment, the suspended elements forming resonators may be plates or discs vibrating according to volume deformation modes, for example in extensional mode.

FIG. 7 shows one such example embodiment. The vibrating element 404 of the sensor C3 is formed by a disc suspended by two diametrically opposite straight beams 414. The sensor comprises excitation means 408 of the electrostatic type formed by electrodes supported by the substrate 2 across from an edge of the disc 404 on one side of the suspension beams 414. These excitation means generate a movement in the plane of the substrate. The sensor also comprises detection means 412 of the capacitive type formed by electrodes supported by the substrate across from the other edge of the disc 404 on the other side of the suspension beams 414. The capacitive detection means 412 have the advantage of avoiding having a mechanical connection between the vibrating element 404 and the support 2, which reduces heat losses. Furthermore, this makes it possible to have less noise upon detection, but the elements are a bit thicker, about of the order of μs to 10 μs, and have a greater thermal inertia.

Figures 8A, 8B, 8C:
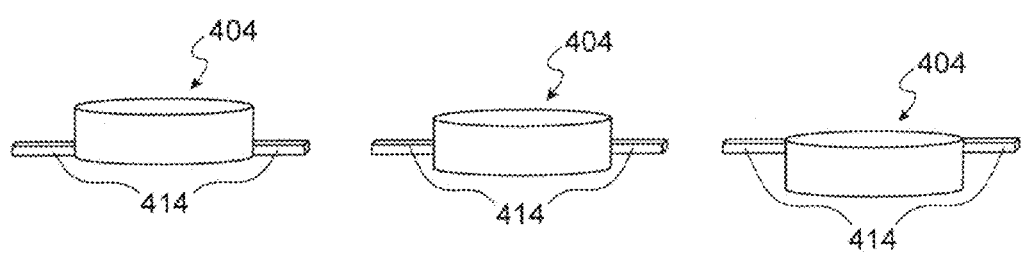
FIGS. 8A to 8C are alternative embodiments of the vibrant element adapted to the sensor of FIG. 7.

As shown in FIGS. 8A to 8C, the thickness of the vibrating elements may be different from those of the suspension beams, which makes it possible to produce suspension beams having a small section to reduce the heat losses. As an example, the vibrating elements may have a thickness of from 100 nm to 5 μm and the beams may have a thickness of from 10 nm to 100 nm. The diameter of the disc may be comprised between 1 μm and 100 μm.

In the illustrated example, the vibrating element forms resonators in the shape of a disc, but other shapes are also possible, for example a square shape, a rectangular shape, or an annular or rectangular or even square frame shape.

The heating means 410 are advantageously formed by the suspension beams 414, which are polarized and ensure heating by Joule effect.

The implementation of capacitive detection means further has the advantage of minimizing the Johnson noises that will then only result from the electrical connections. Thus, a vibrating beam with electrostatic actuation and capacitive detection may also be considered by using the first electrode for actuation and the second electrode for detection, for example.

Figure 13A:
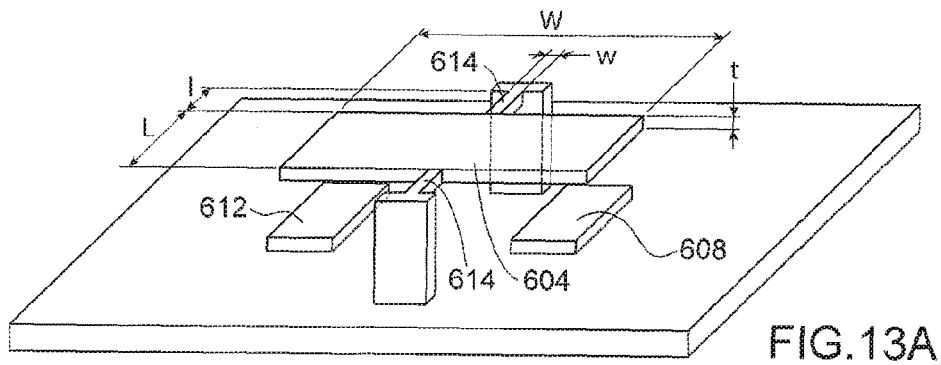
FIGS. 13A and 13B are top and side views of an example embodiment in which the vibrating element is a rotating plate.
Figure 13B:
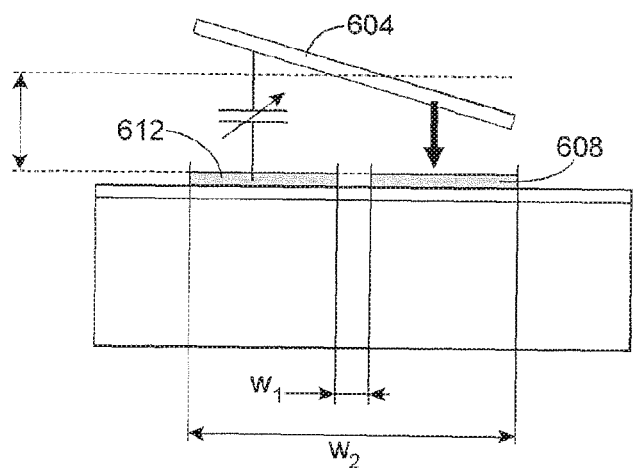

Alternatively, it is possible to consider excitation means as they generate a movement of the suspended element perpendicular to the plane of the substrate, called out-of-plane movement, to be opposed. An example embodiment of such a sensor is shown in FIGS. 13A and 13B. In this example, the vibrating element 604 is a plate rotating around an axis of rotation formed by two suspension beams 614 stressed in torsion, formed by metal wires. A first electrode 608 is placed below the vibrating element on the substrate so as to excite the vibrating element. A second electrode 612 is provided next to the first electrode to ensure capacitive detection. Alternatively, the two electrodes participating in the excitation, and at given time intervals, detection is done by one or both electrodes.

The electrodes are formed either by a metal deposit or by stronger localized doping. The vibrating plate may be made from monocrystalline silicon. The electrodes are for example made from doped AlSi.

The embeddings may be done in the same material or another material, for example a thermally insulating material such as SiN; in that case, a fine metal layer is deposited on the embedding(s) to ensure electrical contact for minimizing heat losses. The embeddings may be nanostructured so as to provide improved thermal insulation, as described above.

As an example, the structure of FIG. 11 may have the following dimensions:

detection means. To that end, the strain applied on the suspension beams, at least one, and preferably two, of which also form strain gauges, is detected. The operation is then similar to that of FIG. 1. The gauges also form the heating means. Alternatively, it is possible to provide some suspension beams dedicated to heating and others dedicated to piezoresistive detection.

This embodiment implementing a vibrating element in the form of a plate has the advantage of offering a large heat exchange surface with the gaseous environment.

According to a second embodiment of a sensor according to the invention, the heating means are situated away from the vibrating element and the heating takes place by conduction through the gaseous environment.

Figure 9:
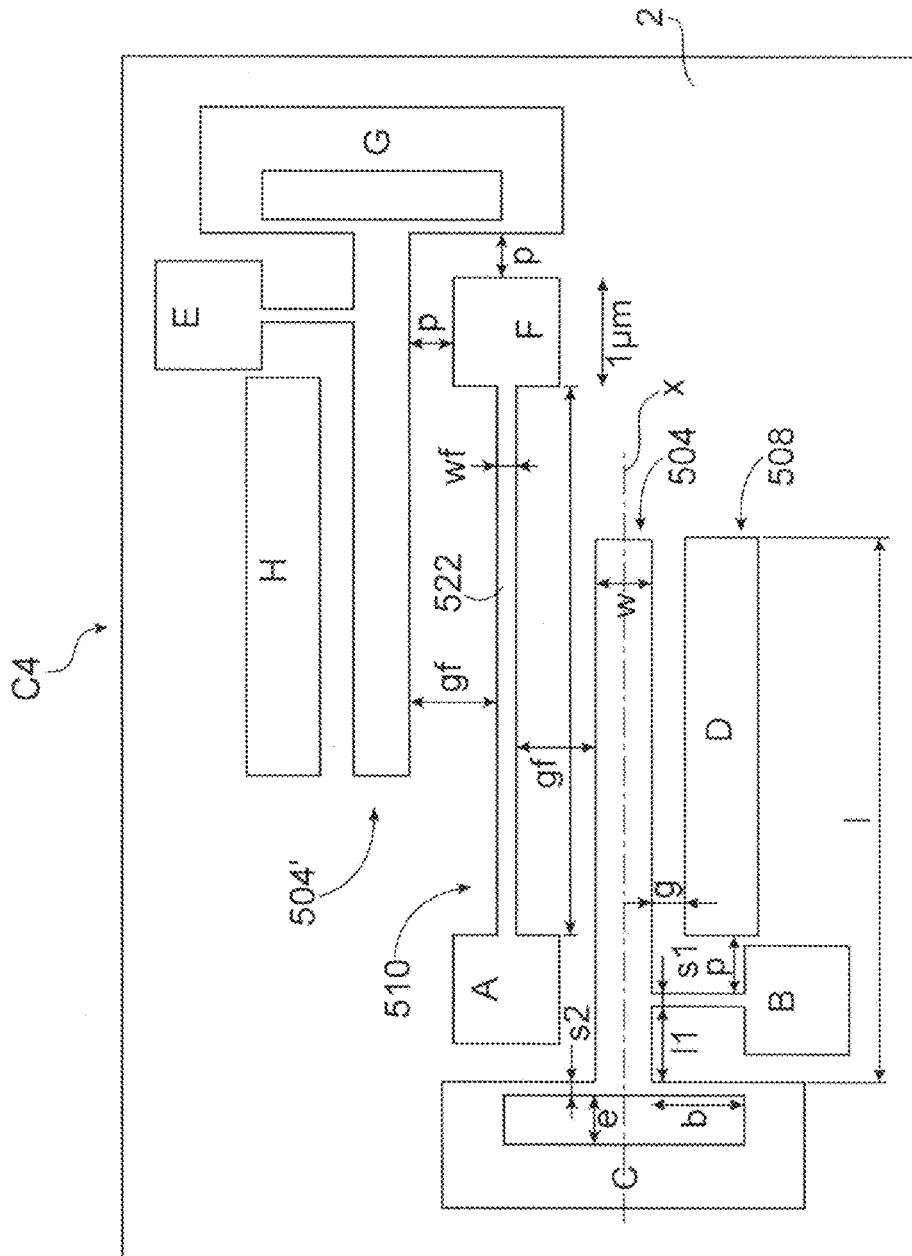
FIG. 9 is a diagrammatic top view of a sensor according to a second embodiment.

FIG. 9 shows an example embodiment of a sensor according to the second embodiment, the sensor C4 further having the particularity of comprising two suspended elements 504, 504'.

We will describe the vibrating element 504 and the means associated with it in detail; this description also applies to the vibrating element 504'.

The vibrating element 504 and the associated means are close to those of the sensor of FIG. 1. The vibrating element 504 is made up of a beam with a longitudinal axis X suspended by one of its ends at the substrate by two beams 514 aligned along an axis Y perpendicular to the axis X. Electrostatic excitation means 508 are provided; they comprise an electrode facing a lateral edge of the vibrating element 504. The detection means are formed by a piezoelectric gauge 520 suspended between the vibrating element and a stud B and extending along an axis Y perpendicular to the longitudinal axis X.

The sensor C4 comprises heating means 510 formed by a suspended wire 522 between two anchoring studs advantageously forming contact studs; the wire 522 is situated at a distance gf from the vibrating element 504. Preferably, the wire 522 is parallel to the vibrating element 504 so as to ensure homogenous heating of the vibrating element 504 over its entire length.

| Parameters | L | W | l | w | $W_1$ | $W_2$ | $L_{elec}$ | t | Gap |
|---|---|---|---|---|---|---|---|---|---|
| Typical values | 12 μm | 12 μm | 1 μm | 50 nm | w | 0.8 W | L | 50 nm | λ/4 |

L being the width of the vibrating plate;
W being the length of the vibrating plate;
l being the length of the suspension beams;
t being the thickness of the vibrating plate and the gauges;
w being the width of the suspension beams;
w2 being the distance separating the two opposite faces of the electrodes;
w1 being the distance separating the two opposite faces of the electrodes;
Gap being the distance between the axis of rotation and the free face of the electrodes across from the vibrating plate.

The excitation voltage and the polarization voltage for heating that are applied are approximately from 1 V to 20 V. This is a direct voltage that may allow both excitation and heating. It is then possible to perform an actuation at frequency w/2, without applying a direct voltage, in which case the voltage only provides heating. If the heating and excitation require a voltage of the same order of magnitude, that voltage may be used for both; otherwise, actuation is done at w/2 and the direct voltage is effective only for heating.

The suspension beams described above relative to FIGS. 6A to 6C may be used to suspend the resonator of FIG. 7.

Alternatively, it is possible to consider a sensor implementing a resonator made up of a vibrating element according to volume deformation modes comprising piezoresistive It will be understood that the suspended wire 522 may not be linear, but may have shapes adapted to the bulk of the sensor, for example in a zigzag or other shape, like those illustrated in FIGS. 6A to 6C.

The vibrating element 504' is positioned across from the vibrating element 504 relative to the wire 522 that extends along a longitudinal axis parallel to the axis X. Preferably, the same distance separates the vibrating element 504' from the wire 522 and the vibrating element 504 from the wire 522 so as to allow differential measurement and simplify measurements.

As in the first embodiment, the suspension means and the gauges have small sections so as to reduce the heat losses from the suspended elements 504, 504' toward the substrate.

The operation of the sensor C4 is similar to that of the sensor C1 except for the heating of suspended elements. In fact, in this embodiment, the suspended elements are heated by propagation of the heat between the wire 522 and the suspended element(s) 504, 504' primarily by heat conduction through the gas to be analyzed.

The table below provides an example of dimensioning of the sensor C4.

It may in particular constitute the second thick layer for structures having two thicknesses.

The suspended structure may also be covered with a metal (for example Al, AlSi, TiN).

A sensor according to the invention with a suspended structure in which the vibrating element has a thickness greater than that of the gauges and suspension beams may

| w | l | l1 | b | s1 | s2 | e | p | gf | lf | wf | gf | g |
|---|---|----|---|----|----|----|----|----|----|----|----|----|
| 300 nm | 3.2 μm | 480 nm | 300 nm | 100 nm² | 120 nm² | 250 nm | 250 nm | 750 nm | 3.2 μm | 100 nm | 200 nm | 150 nm | w is the width of the suspended elements 504, 504';
l is the length of the suspended elements 504, 504';
l1 is the distance between the gauge 520 and the beam 514;
b is the length of the beam 514, which is also the length of the gauge 520;
s1 is the section of the gauge 520;
s2 is the section of the beams 514;
e is the distance between the anchoring stud C and the lateral edge across from the beams 514;
p is the distance between the gauge 20.1 and the electrode D;
g is the distance between the electrode and the lateral face across from the vibrating element 4;
gf is the distance between the wire 522 and the lateral face across from the vibrating element 504; gf may be comprised between 100 nm and 1 μm as a function of the bulks of the studs;
lf is the length of the wire 522;
wf is the width of the wire 522.

This embodiment may have a higher detection efficiency, since the properties of the gas participate in the heating of the suspended elements. The frequency resolutions and the temperature resolutions may be calculated as for the sensor C1.

The example embodiment of FIG. 9 implementing two suspended elements has the advantage of having access to a differential measurement making it possible to facilitate reading, since the residual continuous background effect is eliminated, such as the slow temperature variations distinct from those due to the heating means and the heat exchanges with the gaseous environment.

It is also possible to produce a sensor C4 according to the second embodiment only having a single vibrating element. However, this sensor does not make it possible to perform a differential measurement.

Alternatively, two gauges may be provided per vibrating element.

Elements vibrating according to deformation modes may be implemented in the sensor structure according to the second embodiment. This embodiment would nevertheless have a greater bulk than the sensor of FIG. 9.

By multiplying the vibrating elements, it is possible to increase the resolution of the sensor. This method consists of taking a spatial average of the noise over a large number of samples, thereby reducing the noise by a factor $\sqrt{n}$.

Such a measuring device comprises n sensors; one thus obtains a measuring device whereof the resolution is increased. The sensors are associated by cross connections, preferably implementing at least two metallization levels.

By considering the same actuating voltage and the same reading current in each of the sensors, the placing n frequency sensors in parallel makes it possible to reduce the Johnson and Flicker noises. The matrices of sensors thus produced may be addressed collectively, i.e., by using an input and an output for a network, or addressed individually, i.e., each sensor having its own actuation and reading.

The suspended structure may be produced from different materials, for example N or P doped silicon, Ge, SiGe. Advantageously, porous silicon may be used so as to increase the heat exchange surface of the vibrating element.

for example be made using a method similar to that described in document EP 1840582.

FIGS. 10A to 10H share diagrammatic illustrations of the different steps of a production method.

Figure 10A:
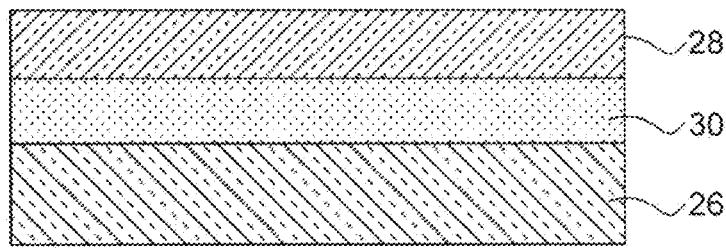
FIGS. 10A to 10H are diagrammatic illustrations of different steps of an example of a method for producing a sensor according to the invention.

In the described example, a SOI (Silicon On Insulator) plate is used, shown in FIG. 10A. The SOI substrate comprises a layer of silicon 26 and a layer of monocrystalline silicon 28, the layers 26, 28 being separated by a layer of $SiO_2$ 30. The layer of monocrystalline silicon 28 forms the front face.

Figure 10B:
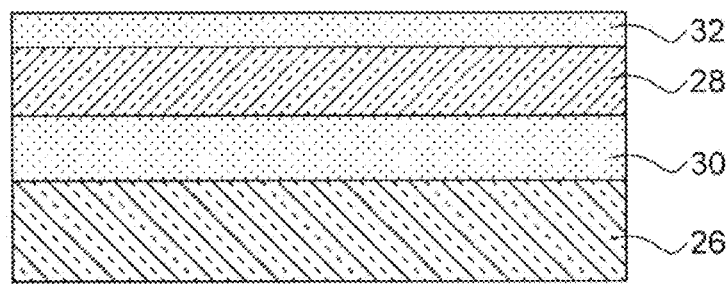

During the first step, an oxide layer of $SiO_2$ 32 is deposited on the layer 28. The element thus formed is shown in FIG. 10B.

During a subsequent step, a P++ doping is done, for example with boron, of the silicon layer 28 situated between the oxide layer 30 and the oxide layer 32.

The doping through the oxide layer allows more homogenous distribution of the dopants in the layer 28. The obtained doping is approximately $1 \cdot 10^{19}$ at./cm³. This doping results in maximizing the temperature coefficient of resistance of the silicon.

Figure 10C:
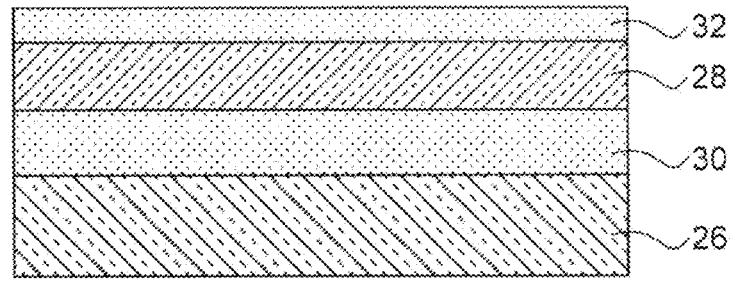

The element thus formed is shown in FIG. 10C. The doping is symbolized by dots.

During a subsequent step, the oxide layer 32 is removed and a layer of resin 33 is deposited, in which the contours define patterns in the resin 32 by lithography, for example deep UV (DUV) lithography or DUV and electron beam (e-beam) hybrid lithography. These lithography methods are well known by those skilled in the art will not be described in detail. E-beam lithography makes it possible to eliminate the effects related to diffraction of the light during the etching of nanometric devices.

Figure 10D:
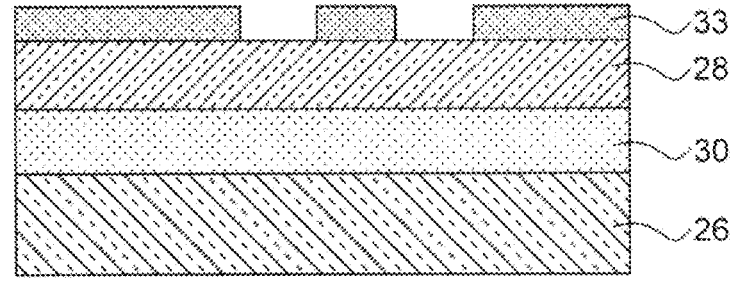

The element thus formed is shown in FIG. 10D.

During a subsequent step, the silicon layer is etched, for example by anisotropic reactive ion etching (RIE).

Figure 10E:
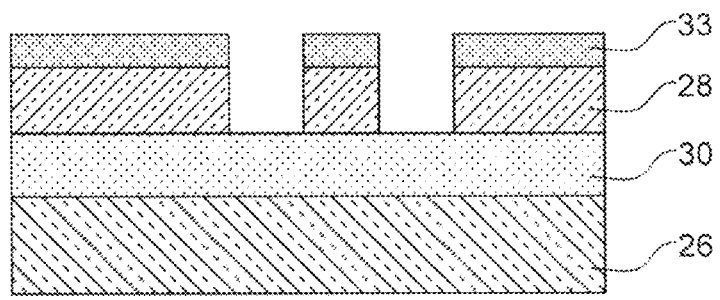

The element thus formed is shown in FIG. 10E.

Figure 10F:
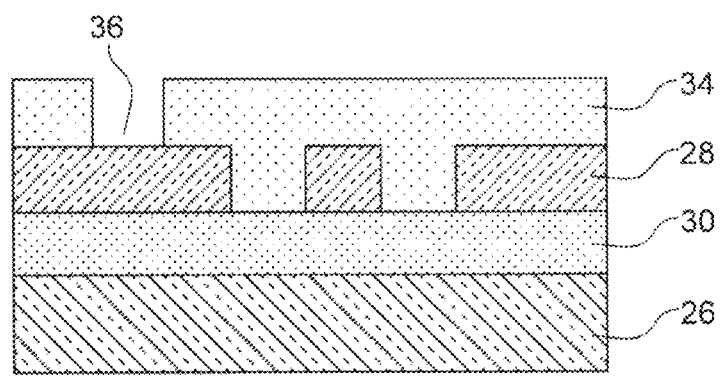

During a subsequent step, an $SiO_2$ chemical deposition 34 is done on the etched silicon layer 28, which is then etched, for example by plasma etching, to delimit the locations 36 of the electrical contacts. The element thus obtained is shown in FIG. 10F.

Optionally, it is possible to perform two additional lithography (for example, e-beam) and reactive ion etching (RIE) steps to nanostructure the silicon on the embedding zones of the suspensions and/or gauges, in the example embodiment of FIG. 12.

Figure 10G:
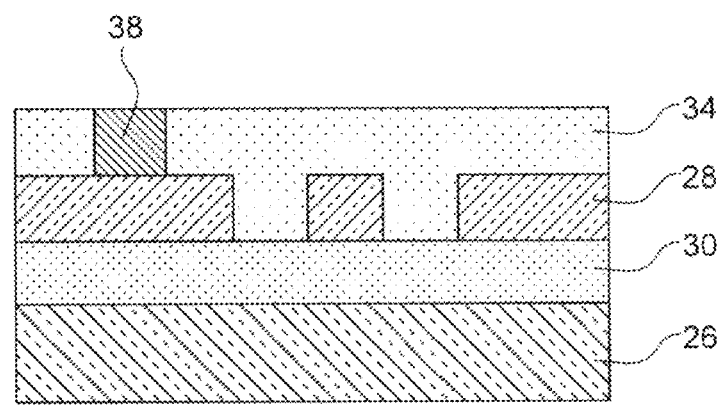

The electrical contacts 38 are next made for example by depositing aluminum, for example by spraying. The element thus obtained is shown in FIG. 10G.

During a subsequent step, the vibrating element is freed, for example by etching the layer 30, for example using hydrofluoric acid vapor.

Figure 10H:
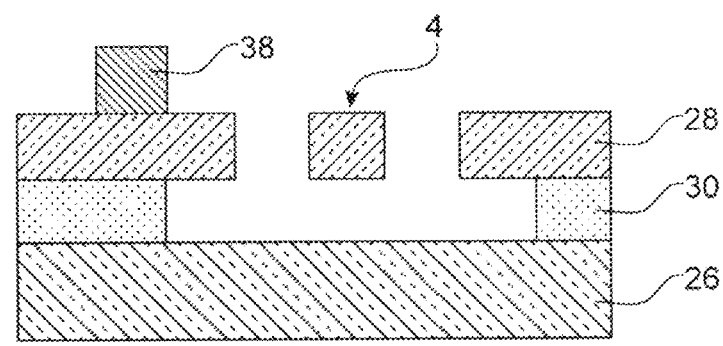

The freed structure is visible in FIG. 10H.

A structure is thus obtained formed from a single block of suspended monocrystalline silicon.

The thermal flow sensor according to the invention makes it possible to produce a gas concentration sensor.

As indicated above, this sensor is particularly suitable for being associated with a gas chromatography micro-column. One or more sensors are positioned in a channel serially connected at the outlet of the micro-column and make it possible to detect the analyte peaks. In fact, the vibrating element thermally insulated from the substrate may have a thermal time constant τth that is smaller than the width of the chromatography peaks, preferably by at least a factor 10.

The invention claimed is:

1. A thermal flow sensor comprising:
a support,
at least one vibrating element capable of being vibrated relative to the support,
suspension and thermal insulation elements for insulating the at least one vibrating element relative to the support,
a heater for heating the at least one vibrating element,
an electric field excitation device which excites by an applied electric field the at least one vibrating element so as to vibrate the at least one vibrating element at a resonance frequency of the at least one vibrating element, and
a detector for detecting a resonance frequency variation of the at least one vibrating element caused by a temperature variation of the at least one vibrating element due to heat exchanges with a surrounding gas.

2. The thermal flow sensor according to claim 1, wherein the suspension and thermal insulation elements comprise at least one beam extending primarily in one dimension.

3. The thermal flow sensor according to claim 1, wherein the suspension and thermal insulation elements comprise at least two beams aligned on either side of the at least one vibrating element or inclined relative to one another and having a common link to the at least one vibrating element.

4. The thermal flow sensor according to claim 2, wherein the at least one beam has a section comprised between $10 \times 10$ nm$^2$ and $250 \times 250$ nm$^2$.

5. The thermal flow sensor according to claim 2, wherein the at least one beam has a nonlinear shape.

6. The thermal flow sensor according to claim 2, wherein the at least one beam is made from a thermally insulating material.

7. The thermal flow sensor according to claim 1, wherein the suspension and thermal insulation elements comprise a zone for anchoring to the support, formed by a nanostructured material.

8. The thermal flow sensor according to claim 1, wherein the heater heats the at least one vibrating element by Joule effect.

9. The thermal flow sensor according to claim 8, wherein the heater is in direct contact with the at least one vibrating element.

10. The thermal flow sensor according to claim 9, wherein the heater is formed by at least one electrically conducting element connected to a polarization source and the at least one vibrating element.

11. The thermal flow sensor according to claim 1, wherein the detector is formed by at least one piezoresistive gauge mechanically connected to the at least one vibrating element.

12. The thermal flow sensor according to claim 11, wherein the heater is formed by at least one electrically conducting element connected to a polarization source and the at least one vibrating element and wherein said at least one piezoresistive gauge forms a Joule effect heater.

13. The thermal flow sensor according to claim 1, wherein the heater is situated separated from the at least one vibrating element, the heating being obtained by conduction through a gaseous environment between the heater and the at least one vibrating element.

14. The thermal flow sensor according to claim 13, wherein the heater is formed by a suspended wire.

15. The thermal flow sensor according to claim 13, comprising two vibrating elements positioned on either side of the heater so as to perform a differential measurement.

16. The thermal flow sensor according to claim 1, wherein the at least one vibrating element has volume deformation modes won excitation.

17. The thermal flow sensor according to claim 1, wherein the at least one vibrating element is at least one rotational vibrating element.

18. The thermal flow sensor according to claim 1, wherein the detector comprises two piezoresistive gauges providing a differential measurement.

19. The thermal flow sensor according to claim 1, wherein the detector is a capacitive detector.

20. The thermal flow sensor according to claim 1, wherein the electric field excitation device comprises an electrostatic excitation device.

21. A thermal flow measuring system comprising a plurality of sensors according to claim 1.

22. A system for determining the concentration of a gaseous environment comprising at least one thermal flow sensor according to claim 1 or a system according to claim 21, and electronics for processing electrical voltage values delivered by the thermal flow sensor.

23. The determination system according to claim 22, wherein the at least one thermal flow sensor is placed in an electronic oscillating and frequency- or phase-measuring loop.

24. A device for analyzing a gas or mixture of gases comprising a gas chromatography column and at least one system for determining the concentration according to claim 23, said determination system being positioned in a channel connected to an outlet of the gas chromatography column.

25. A method for measuring thermal flow, comprising:
measuring in a single measurement a resonance frequency variation of at least one vibrating element caused by a temperature variation of the at least one vibrating element due to heat exchanges with a surrounding gas, the at least one vibrating element belonging to a thermal flow sensor which comprises:
a support of the at least one vibrating element which is capable of being vibrated relative to the support,
suspension and insulation elements for insulating the at least one vibrating element relative to the support, a heater for heating the at least one vibrating element, an electric field excitation device which excites by an applied electric field the at least one vibrating element so as to vibrate the at least one vibrating element at a resonance frequency thereof, a detector for detecting the resonance frequency variation of the at least one vibrating element caused by a temperature variation of the at least one vibrating element due to the heat exchanges with the surrounding gas.

26. The thermal flow sensor according to claim 3, wherein the at least two beams have a section comprised between $10\times10$ nm$^2$ and $250\times250$ nm$^2$.

27. The thermal flow sensor according to claim 3, wherein the at least two beams have a nonlinear shape, a serpentine shape, or a shape with at least one rectangle that is hollow between two segments.

28. The thermal flow sensor according to claim 3, wherein the at least two beams are made from a thermally insulating material.

29. The thermal flow sensor according to claim 2, wherein the at least one beam has a serpentine shape.

30. The thermal flow sensor according to claim 2, wherein the at least one beam has a shape with at least one rectangle that is hollow between two segments.

\* \* \* \* \*